US00PP12221P2

(12) United States Plant Patent
Small

(10) Patent No.: US PP12,221 P2
(45) Date of Patent: Nov. 27, 2001

(54) STRAWBERRY PLANT NAMED 'CAL GIANT 2'

(75) Inventor: David W. Small, Arroyo Grande, CA (US)

(73) Assignee: Calfifornia Giant, Inc., Watsonville, CA (US)

( * ) Notice: Subject to any disclaimer, the term of this patent is extended or adjusted under 35 U.S.C. 154(b) by 0 days.

(21) Appl. No.: 09/379,679

(22) Filed: Aug. 24, 1999

(30) Foreign Application Priority Data

Oct. 7, 1998 (EP) ..... 98/1349

(51) Int. Cl.[7] ..... A01H 5/00
(52) U.S. Cl. ..... Plt./209
(58) Field of Search ..... Plt./208, 209

(56) References Cited

U.S. PATENT DOCUMENTS

| | | | |
|---|---|---|---|
| P.P. 5,262 | 7/1984 | Voth et al. | Plt./48 |
| P.P. 5,266 | 7/1984 | Bringhurst et al. | Plt./49 |
| P.P. 7,614 | 8/1991 | Bringhurst et al. | Plt./49 |
| P.P. 8,708 | 5/1994 | Voth et al. | Plt./49 |
| P.P. 9,320 | 10/1995 | Small et al. | Plt./49 |
| P.P. 10,451 | 6/1998 | Shaw | Plt./49 |
| P.P. 10,461 | 6/1998 | Shaw | Plt./49 |
| P.P. 10,960 | 6/1999 | Lopez | Plt./208 |
| P.P. 10,982 | 6/1999 | D'Ercole et al. | Plt./208 |

*Primary Examiner*—Bruce R. Campell
*Assistant Examiner*—Michelle Kizilkaya
(74) *Attorney, Agent, or Firm*—David A. Farah; Sheldon & Mak

(57) ABSTRACT

A new distinct variety of strawberry plant that produces equivalent yields of equally high quality fruit in both fumigated and non-fumigated conditions, is resistant to many common foliar and soil borne diseases and pests and has unusually excellent fruit flavor and aroma.

4 Drawing Sheets

CROSS-REFERENCE TO RELATED APPLICATION

This application takes priority from co-pending European Community Plant Protection Application No. 98/1349, filed Oct. 7, 1998, the contents of which are incorporated herein in their entirety.

BACKGROUND OF THE INVENTION

This new variety of strawberry, named 'Cal Giant 2', resulted from a cross performed in 1992 between a proprietary plant designated A43 and the cultivar Chandler (U.S. Plant Pat. No. 5,262). The proprietary plant A43 was maintained exclusively for breeding purposes, was not released to growers, and has not been the subject of an application for a plant patent in the United States.

'Cal Giant 2' was first selected as a seedling variety at a breeding test plot in Santa Maria, Calif. and has been propagated asexually by runners in Susanville, Calif. and Malin, Oreg. It was originally designated, '48C123' and later designated as advanced selection, 'C98'. Asexual propagules from this original source have been tested at test plots in Oxnard, Santa Maria, and Watsonville, Calif. This propagation and testing has demonstrated that the combination of traits disclosed herein which characterize propagules of 'Cal Giant 2' are fixed and retained true to type through successive generations of asexual reproduction.

SUMMARY OF THE INVENTION

'Cal Giant 2' is a new and distinct strawberry variety characteristically different from any other strawberry variety. Among the characteristics that distinguish 'Cal Giant 2' are a combination of traits which include a strong everbearing tendency; natural resistance to many pests and foliar, fruit, and root diseases; production of a high number of exceptionally sweet fruit that are smoother and straighter than other commerical varieties. In addition, 'Cal Giant 2' produces equivalent yields of equally high quality fruit in both fumigated and non-fumigated conditions, and its fruit pollinates well in inclement weather conditions, allowing for continued production of well shaped, marketable fruit following cold and moist conditions.

BRIEF DESCRIPTION OF THE FIGURES

The accompanying color photographs show typical specimens of the new strawberry variety designated 'Cal Giant 2', including fruit, foliage and flower, as follows.

DETAILED BOTANICAL DESCRIPTION OF THE NEW VARIETY

Color terminology used herein is in accordance with the PANTONE®Color Formula Guide 1000 (Pantone Inc., 590 Commerce Boulevard, Carlstadt, N.J. U.S. 07072-3098). The color descriptions and color illustrations are as nearly true as is reasonably possible. However, it is understood that both color and other phenotypic expressions described herein may vary from plant to plant with differences in growth, environmental and cultural conditions, without any change in the genotype of the variety 'Cal Giant 2'.

Unless specified otherwise, the 'Cal Giant 2' plants described below are for plants in mid-July, the month of an annual planting scheme, and primary fruit are described.

Botanical Classification and Parentage

'Cal Giant 2' is a member of the genus Fragaria and species *ananassa*. It is a cross between a proprietary plant designated 'A43', a female, and the cultivar 'Chandler', a male.

Physical Description

Figure 1:
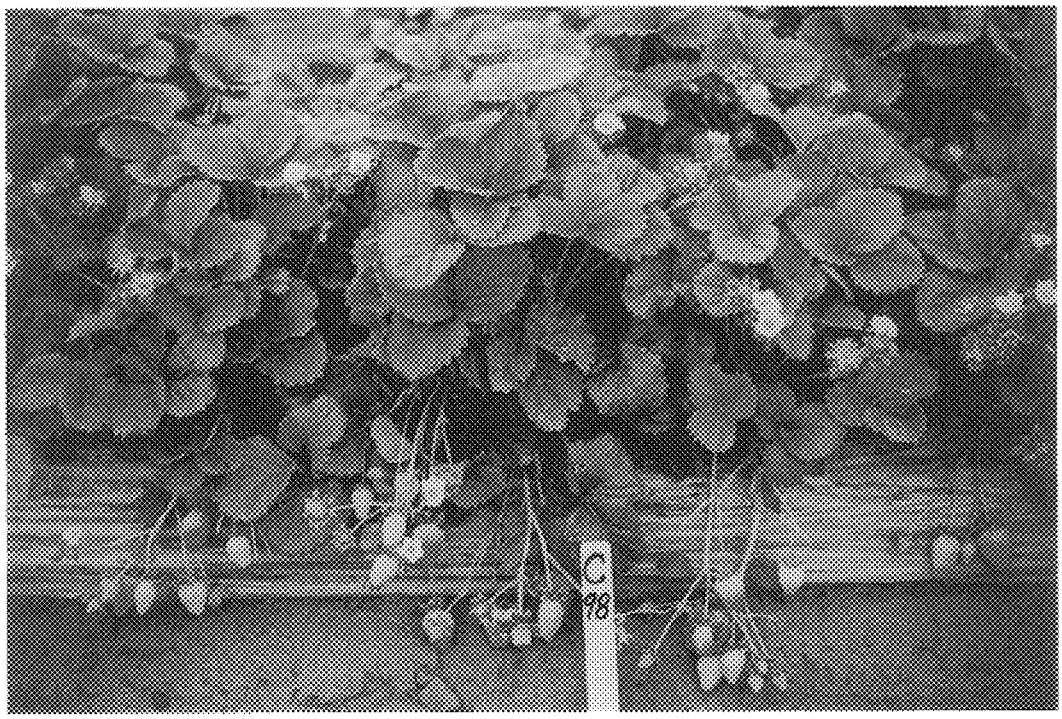
FIG. 1 is a color photograph taken July 1998 showing the general plant architecture, flowering, and fruiting characteristics of plants grown in a standard, fumigated, cultural system.

Referring now to FIG. 1, there is shown a color photograph taken in July 1998 showing the general plant architecture, flowering, and fruiting characteristics of plants grown in a standard, fumigated, cultural system. As can be seen, fruiting plants of 'Cal Giant 2' grow in a semi-erect habit. 'Cal Giant 2' plants are more dense and not as large as 'Catalina' (U.S. Plant Pat. No. 9,320), and are more erect and open than 'Selva' (U.S. Plant Pat. No. 5,266).

As can be seen further in FIG. 1, the buds and fruit of 'Cal Giant 2' develop well away from the plant, advantageously easing harvest and allowing for good ventilation which reduces the incidence of fruit diseases. In general, 'Cal Giant 3' achieves a mid to late-season height of approximately 35 cm and a spread of approximately 70 cm. 'Cal Giant 2' has an upright fruiting habit with trusses that droop to the shoulder of the bed as fruit ripens, and that average 30.9 cm in length. Average peduncle length is 30.9 cm. Average length between the peduncle the crown and the pedicel connection is 20.85 cm. Average length of the pedicel from the peduncle connection to the basal connection of the fruit is 5.19. Inflorescence length is longer than 'Camarosa' (U.S. Plant Pat. No. 8,708) and 'Selva', and shorter than 'Catalina' and 'Chandler'. The inflorescence tends to elongate as the plant grows larger throughout the season.

'Cal Giant 2' plants have mid-season leaf petioles averaging 25.1 cm in length, making them more vigorous through mid-season than 'Selva' plants and less vigorous through mid-season than 'Catalina' and 'Seascape' U.S. Plant Pat. No. 7,614) plants. Mid-season leaf petiole diameter averages 3.88 mm in width. Mid-season ternate (or trifoliate) leaves average 17.15 cm in width (measured across the widest area of the ternate leaf) and 10.85 cm in length (measured from the basal ternate connection to the primary leaf tip).

Leaf stipules are markedly winged and average 3.36 cm in length from the base of the petiole to the tip of the stipule. Mature stipules display a light, reddish to brown color at the tip.

Figure 2:
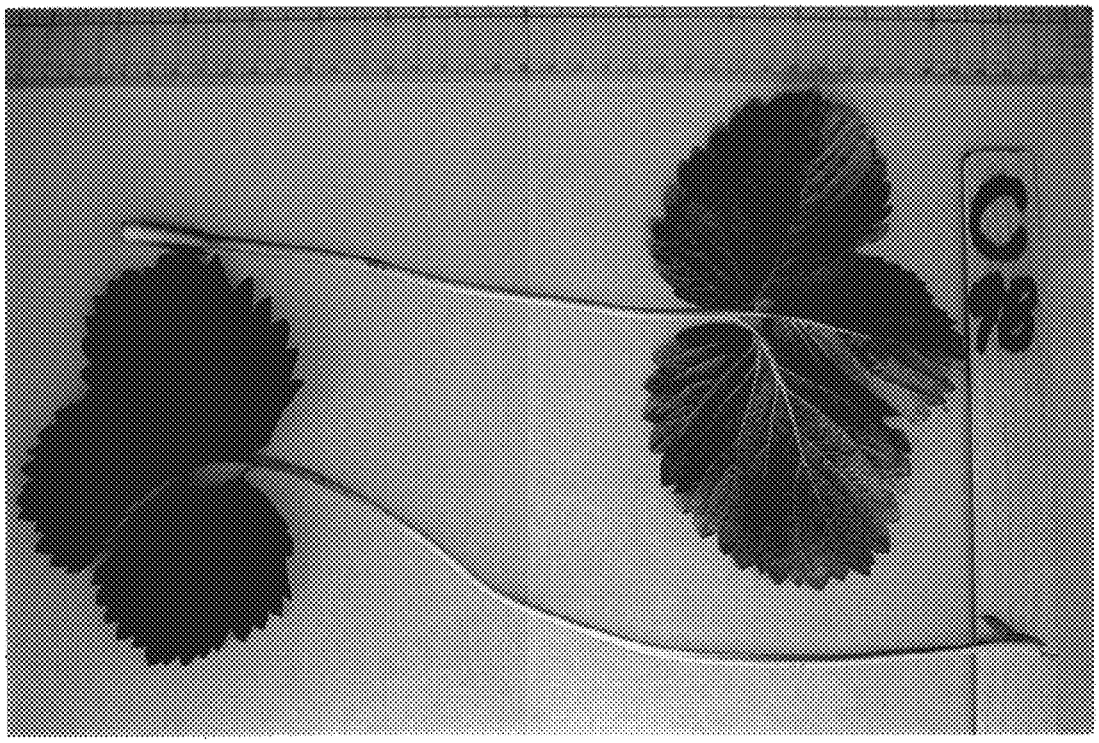
FIG. 2 is a color photograph showing a close-up view of the abaxial and adaxial aspects of typical mature mid-season leaves.

The leaves of 'Cal Giant 2' appear strong and healthy with new leaves appearing above the existing canopy throughout the growing season. 'Cal Giant 2' canopy density is open. Referring now to FIG. 2, there is shown a color photograph showing a close-up view of the abaxial aspects of typical mature mid-season leaves. As can be seen, leaves of 'Cal Giant 2' have a shiny, waxy cuticle and about 15 to 18 serrations per leaflet. 'Cal Giant 2' plant leaves tend to be medium to dark green in color, similar to 'Camarosa' and 'Selva' plant leaves, and are darker than both 'Catalina' plant leaves and 'Chandler' plant leaves. Visual comparisons of 'Cal Giant 2' leaf color to 'Catalina', 'Camarosa', and 'Chandler' leaf colors were made using the PANTONE200 Color Formula Guide 1000 (Pantone Inc., 590 Commerce Boulevard, Carlstadt, N.J., U.S. 07072-3098) and the results are given in Table I, below.

Further as can be seen in FIG. 2, each of the three leaflets per leaf tend to be slightly rugose, flat and orbicular in shape, with dentate leaf margins. The leaflet base is truncate. The leaflet apice is mucronate. Further, leaflets of 'Cal Giant 2' are more orbicular than leaflets of 'Catalina' or 'Seascape'.

'Cal Giant 2' plants display bract leaves on less 5% of petioles. The bract leaves occur individually. The presence or absence of bract leaves and their size do no appear to be related to the stage of development of the primary leaves or to the size of the plant.

Tomentum is very sparsely present on 'Cal Giant 2' leaf petioles. When present, the hairs measure 1 mm or less in length, are perpendicular to the leaf petiole, and in greatest abundance nearest the leaves.

While stolons are not present during the fruiting season, 'Cal Giant 2' runners profusely at plant nurseries in Susanville, Calif. and Malin, Oreg., producing 25 to 30 stolons per mother plant. Stolons produced by 'Cal Giant 2' lack pubescence and any appearance of anthocyanin. Crown size of plants produced along the stolons vary dependent upon stage of development. Average crown diameter of daughter plants produced along the stolons are less than or equal to 1 cm.

The buds, blooms, and fruit are borne on a dichasium cyme whose mid-season length averages 30.9 cm from the crown to the apice of the primary fruit. Each receptacle bears hundreds of pistils. Each flower bears an average of five, completely white, overlapping petals, that average 1.4 cm in length and 1.6 cm in width. There are 20 stamens per bloom, each hearing an anther measuring 1.0–1.4 mm in diameter. The average filament measures 2.8 mm in length. The average mid-season bloom measures 2.75 cm from petal edge to petal edge diametrically. The calyx is nonclasping, slightly to moderately reflexed, and small to medium in size, averaging 3.52 cm in diameter. Each calyx comprises an average of nine sepals that average 1.5 cm in length and 0.80 cm in length and that are either slightly overlapping or do not overlap. The sepals do not cling to the berry. Achene are present.

Figure 3:
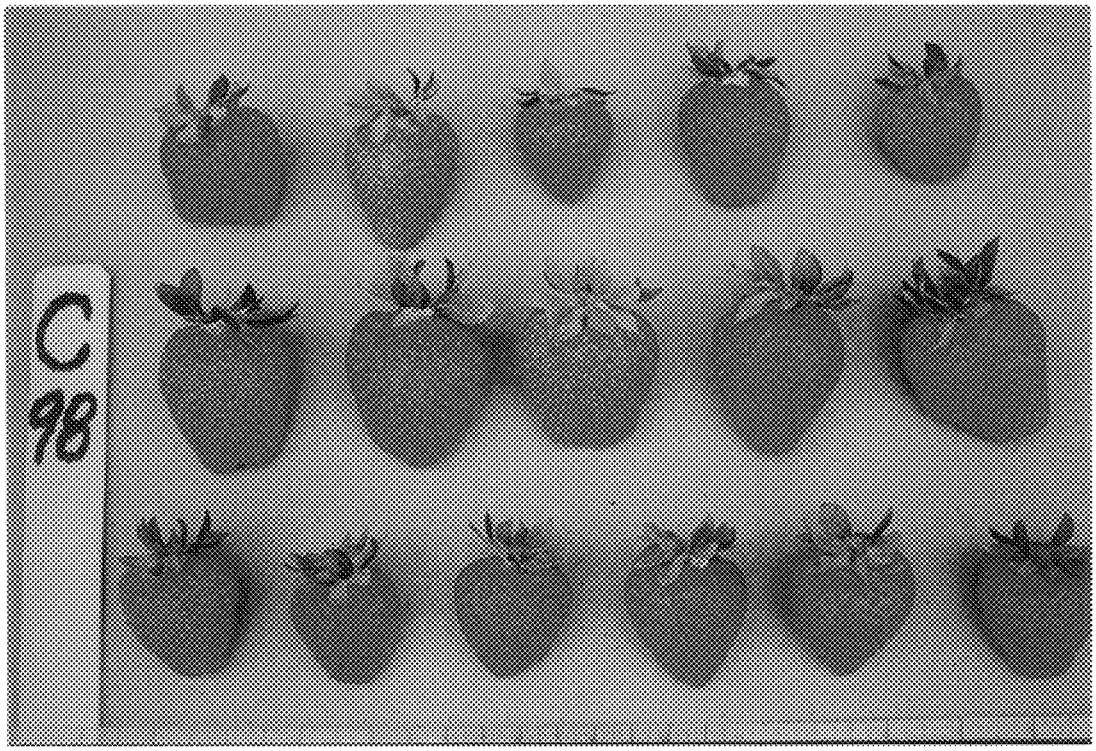
FIG. 3 is a color photograph showing a close-up view of the range of mature whole fruit.

The fruit of 'Cal Giant 2' are initially borne on single stems, branching to dichasium cymes in mid-season. The fruit is medium conic. The fruit is very smooth, significantly smoother down the berry than other commercial varieties currently grown. The ratio of the width of the fruit to the length of the fruit is 4:5. Referring now to FIG. 3, there is shown a color photograph showing a close-up view of the range of mature whole fruit.

'Cal Giant 2' produces a much higher number of well shaped, unblemished fruit than 'Catalina', 'Camarosa', 'Selva', and 'Chandler' varieties. 'Cal Giant 2' fruit average 4.86 cm in length and 3.94 cm in width, and average 30 grams per berry during the season. Advantageously, the difference in the size between primary, secondary and tertiary berries is much less than the difference in many other varieties, such as 'Catalina', 'Chandler' and 'Selva'.

'Cal Giant 3' fruit average 4.86 cm in length and 3.94 cm in width. There is little if any neck on the shoulder of the fruit. The fruit has a very high gloss. Seeds are even with the skin. Seeds range in color from yellow to red, depending on the direction of the fruit in relation to the sun.

The skin an flesh of 'Cal Giant 2' fruit are very firm. The exterior fruit color of 'Cal Giant 2' is a lighter than the exterior fruit color of either 'Catalina' or 'Camarosa'. 'Cal Giant 2' fruit flesh displays good color saturation and the interior color substantially matches the exterior color. Visual comparisons of 'Cal Giant 2' fruit color were made with the fruit color of 'Catalina', 'Chandler' and 'Camarosa' using the PANTONE® Color Formula Guide 1000 and the results are given in Table I, below.

TABLE I

Visual Comparisons of 'Cal Giant 2' Leaf and Fruit Color to 'Catalina', 'Camarosa' , and 'Chandler' Leaf and Fruit Color

| | Adaxial Leaf | Abaxial Leaf | External Fruit | Internal Fruit |
|---|---|---|---|---|
| 'Cal Giant 2' | 363U | 370U | Warm Red U2X | Warm Red U2X |
| 'Camarosa' | 349C | 348U | 193C | 185C |
| 'Catalina' | 343C | 348U–356U | 193C | 185C |
| 'Chandler' | 3435C | 339U | 186C | 179C |

Additionally, the petiole, peduncle, and pedicel color of 'Cal Giant 3' is 360U.

Protein Characteristics

The iso-enzyme content of 'Cal Giant 2' was compared with the iso-enzyme content of five other varieties by gel electrophoresis. The results are given Table II, below.

TABLE II

Comparisons of 'Cal Giant 2' Enzyme Content with the Enzyme Content of 'Aromas', 'Catalina', 'Diamonte', 'Gaviota' and 'Pacifica'

| | Phospho-glucoseisomerase | Leucine-aminopeptidase | Phospho-glucomutase |
|---|---|---|---|
| 'Cal Giant 2' | A3 | B3 | C2 |
| 'Aromas' | A4 | B3 | C2 |
| 'Catalina' | A4 | B3 | C4 |
| 'Diamonte' | A4 | B3 | C2 |
| 'Gaviota' | A2 | B3 | C1 |
| 'Pacifica' | A4 | B3 | C1 |

Flavor and Taste of the Fruit

'Cal Giant 2' has an extraordinarily sweet flavor. The soluble solid content, a measure of sugar content, of 'Cal Giant 2' fruit was determined to be 9.1% using a TY' MUP® 11520-0 ATC Refractometer (TY' MUP PRODUCTS, a Division of Adcock Manufacturing Corporation, Gardena, Calif. 90249), compared to 'Catalina' (8.29%), 'Selva' (8.64%), and 'Chandler' (7.5%). Generally, higher sugar content correlates with better taste.

Resistance to Diseases and Pests

'Cal Giant 2' plants are very healthy, displaying good natural resistance to many foliar, fruit, and root diseases, including Powdery Mildew (*Sphaerotheca macularis* ssp. *fragariae*), Angular Leaf Spot (*Xanthomonas fragariae*), Phomopsis (*Dendrophoma obscurans*), Ramularia (or Mycosphaerella) leaf spot (*Ramularia tulasnet* or *Mycosphaerella fragariae*), as well as some Phytophthora ssp. Further, 'Cal Giant 2' plants are resistant to many fungal diseases of fruit, such as Anthracnos (Colletotrichum spp.) and leather rot (*Phytophthora cactorum*).

Figure 4:
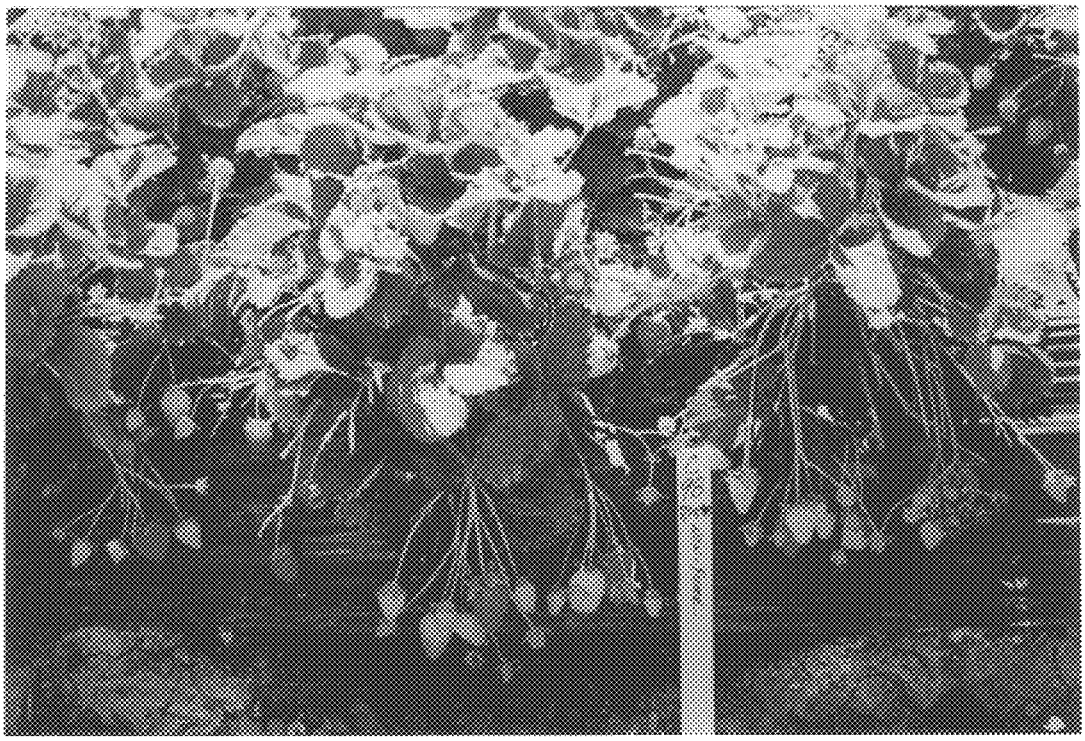
FIG. 4 is a color photograph taken in July 1998 showing the general plant architecture, flowering, and fruiting characteristics of plants grown in a non-fumigated, cultural system.

'Cal Giant 2' has been tested in non-fumigated conditions for several years and has also shown good natural resistance to soil borne diseases such a Verticillium wilt and Phytophothora spp. under these conditions. In non-fumigated conditions 'Cal Giant 2' displays greater resistance to soil borne diseases than 'Aromas' (U.S. Plant Pat. No. 10,451), 'Camarosa', 'Diamonte' (a University of California variety), 'Gaviota' (U.S. Plant Pat. No. 10,461), 'Pacifica' (a University of California variety), 'Seascape' and 'Selva'. Referring now to FIG. 4, there is shown an color photograph of 'Cal Giant 2' during mid-season, successfully growing in non-fumigated conditions.

Productivity Characteristics

'Cal Giant 2' is a strawberry cultivar with a strong everbearing tendency. 'Cal Giant 2' plants are high yielding and produce high quality fruit well into the autumn months. They come into production similar to 'Selva' and 'Seascape' and after 'Catalina' and 'Camarosa', but produce significantly more fruit during the first half of the season than either 'Selva' or 'Seascape'.

'Cal Giant 2' is self-fertile, producing sufficient pollen throughout the season to insure very few malformed fruit. Futher, 'Cal Giant 2' self pollinates well in inclement weather, thus facilitating significant early season production with few discarded fruit due to poor pollination. 'Cal Giant 2' initiates flowers in February in the Santa Maria and Watsonville, Calif. growing areas. Typically, harvest in both the these areas initiates in the second half of March. Production continues in Santa Maria, Calif. Through July, and in Watsonville, Calif. through September. Typical yields of 'Cal Giant 2' in both Santa Maria, Calif. and in Watsonville, Calif. is 23 tons per acre.

Additionally, 'Cal Giant 2' advantageously produces equivalent yields of equally high quality fruit in both fumigated conditions and in non-fumigated conditions. Seasonal production tends to be significantly less cyclic than other commercially grown varieties, gradually building to a mid-season peak, then gracefully dropping in production.

What is claimed:

1. A new and distinct strawberry plant designated 'Cal Giant 2' as herein described and illustrated.

* * * * *